(12) United States Patent
Young et al.

(10) Patent No.: US 10,925,504 B2
(45) Date of Patent: Feb. 23, 2021

(54) METHOD FOR ECG LEAD PLACEMENT CHANGES TO BE ACCURATELY ACCOUNTED FOR

(71) Applicant: General Electric Company, Schenectady, NY (US)

(72) Inventors: Brian J. Young, Wauwatosa, WI (US); Matthew Lane Pemberton, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 239 days.

(21) Appl. No.: 15/409,201

(22) Filed: Jan. 18, 2017

(65) Prior Publication Data

US 2017/0119269 A1    May 4, 2017

Related U.S. Application Data

(63) Continuation of application No. 14/163,831, filed on Jan. 24, 2014, now Pat. No. 9,579,032.

(51) Int. Cl.
*A61B 5/0408* (2006.01)
*A61B 5/044* (2006.01)
(Continued)

(52) U.S. Cl.
CPC .......... *A61B 5/0408* (2013.01); *A61B 5/0402* (2013.01); *A61B 5/044* (2013.01);
(Continued)

(58) Field of Classification Search
CPC .............. A61B 5/04012; A61B 5/0402; A61B 5/04021; A61B 5/0006; A61B 5/7445;
(Continued)

(56) References Cited

U.S. PATENT DOCUMENTS

| | | | | |
|---|---|---|---|---|
| 4,987,901 A | * | 1/1991 | Kunig | A61B 5/04085 600/509 |
| 5,231,990 A | * | 8/1993 | Gauglitz | A61B 5/0006 600/509 |

(Continued)

OTHER PUBLICATIONS

The early recognition f right ventricular infarction: diagnostic accuracy of the electrocardiographic V4R lead:, H.O. Klein et al., Circulation—Journal of the American Heart Association, 1983;67:558-565, http://circ.ahajournals.org/.

(Continued)

*Primary Examiner* — Jennifer Pitrak McDonald
*Assistant Examiner* — Pamela M. Bays
(74) *Attorney, Agent, or Firm* — Andrus Intellectual Property Law, LLP

(57) ABSTRACT

An electrocardiograph system including a monitoring device capable of receiving cardiac signals from electrodes attached to a patient in an alternative electrode configuration, wherein the alternative electrode configuration is one of a predetermined set of known electrode configurations that differs from a default configuration. The system further includes an analysis module configured to analyze the cardiac signals to detect that the electrodes are attached to the patient in an electrode configuration that differs from the default configuration, and then request information from the user identifying the alternative electrode configuration from the predetermined set of known electrode configurations. The analysis module retrieves a set of criteria for assessing the cardiac signals based on the alternative electrode configuration, and automatically analyzes the cardiac signals based on the set of criteria for the alternative electrode configuration.

16 Claims, 7 Drawing Sheets

(51) Int. Cl.
  *A61B 5/04* (2006.01)
  *A61B 5/0402* (2006.01)
  *A61N 1/39* (2006.01)
  *A61N 1/04* (2006.01)
  *A61B 5/00* (2006.01)

(52) U.S. Cl.
  CPC ........ *A61B 5/04012* (2013.01); *A61B 5/0006* (2013.01); *A61B 5/04021* (2013.01); *A61B 5/7445* (2013.01); *A61N 1/0492* (2013.01); *A61N 1/3993* (2013.01)

(58) Field of Classification Search
  CPC .... A61B 5/0408; A61B 5/044; A61N 1/0406; A61N 1/0476; A61N 1/0492; A61N 1/3993
  USPC ......................................................... 600/509
  See application file for complete search history.

(56) References Cited

U.S. PATENT DOCUMENTS

| | | | | |
|---|---|---|---|---|
| 6,282,440 | B1* | 8/2001 | Brodnick | A61B 5/04011 600/512 |
| 7,860,558 | B2* | 12/2010 | Feild | A61B 5/0428 600/509 |
| 2002/0045837 | A1* | 4/2002 | Wei | A61B 5/0006 600/509 |
| 2003/0040305 | A1* | 2/2003 | Ng | A61B 5/0006 455/419 |
| 2003/0171798 | A1 | 9/2003 | Nova et al. | |
| 2003/0233129 | A1* | 12/2003 | Matos | A61B 5/0006 607/5 |
| 2007/0232946 | A1* | 10/2007 | Feild | A61B 5/0424 600/509 |
| 2011/0288605 | A1 | 11/2011 | Kaib | |

OTHER PUBLICATIONS

"Guidelines for the interpretation of the neonatal electrocardiogram", P.J. Schwartz et al., European Heart Journal (2002) 23, 1329-1344.

"ACC/AHA Guidelines for the Management of Patients With ST-Elevation Myocardial Infarction", Antman et al., American College of Cardiology Foundation and the American Heart Association, Inc., 2004.

"Recommendations for the Standardization and Interpretation of the Electrocardiogram: Part I: The Electrocardiogram and Its Technology: A Scientific Statement From the American Heart Association Electrocardiography and Arrhythmias Committee, Council on Clinical Cardiology; the American College of Cardiology Foundation; and the Hearth Rhythm Society Endorsed by the International Society for Computerized Elecrocardiology", Paul Kligfield et al., Circulation—Journal of the American Heart Association, 2007; 115; 1306-1324, http://circ.ahajournals.org/.

* cited by examiner

METHOD FOR ECG LEAD PLACEMENT CHANGES TO BE ACCURATELY ACCOUNTED FOR

CROSS REFERENCE TO RELATED APPLICATION

This application is a continuation of U.S. patent application Ser. No. 14/163,831, filed Jan. 24, 2014, now U.S. Pat. No. 9,579,032, which is incorporated herein by reference in entirety.

BACKGROUND

In cardiac monitoring clinicians often need to vary electrode placement in order to meet specialized physiologic and/or monitoring needs of a patient. In electrocardiography (ECG), for instance, clinicians often utilize electrode configurations other than the standard 12 lead ECG. For example, some clinical guidelines suggest the use of right-sided chest (precordial) leads for pediatric and neonatal applications. Schwartz, P. J., et al. "Guidelines for the Interpretation of the Neonatal Electrocardiogram: A Task Force of the European Society of Cardiology." *European Heart Journal* 23 (2002): 1329-1344. Likewise, right-sided chest (precordial) leads may be used in clinical applications relating, to detection and treatment of certain myocardial infarctions (heart attacks). Antman, Elliott M., et al. "ACC/AHA Guidelines for the Management of Patients with ST-Elevation Myocardial Infarction." *ACC/AHA Practice Guidelines* (2004); Kligfield, Paul, et al. "Recommendations for the Standardization and Interpretation of the Electrocardiogram: Part I: The Electrocardiogram and Its technology: A Scientific Statement From the American Heart Association Electrocardiography and Arrhythmias Committee, Council on Clinical Cardiology; the American College of Cardiology Foundation; and the Heart Rhythm Society Endorsed by the International Society for Computerized Electrocardiology." *Circulation, Journal of the American Heart Association* 115 (2007): 1306-1324. Additionally, some clinical guidelines suggest the use of posterior leads for posterior myocardial infarctions. Id. Moreover, clinicians may use an alternative lead placement for a host of other reasons, including patient injury, such as a lesion at the site of standard electrode placement, and dextrocardia.

Current cardiac monitoring systems, including ECG systems, do not account for such alternative electrode placements that differ from a standard placement, and the systems do not automatically adjust their processing of the cardiac signal to correspond with the alternative electrode placement. Thus, current systems often misanalyze cardiac signals recorded from electrodes in alternative configurations because they analyze the signal as if it were recorded using, a default, or standard, configuration, which results in the system providing inaccurate interpretations of the cardiac signal and incorrect suggestions for diagnoses.

SUMMARY

The present inventors recognize that the current systems and methods of electrocardiographic (ECG) monitoring, as well as other monitoring and diagnostic systems and methods do not detect changes in electrode placement from standard configurations to other known configurations that are clinically useful or non-standard electrode placement that is medically necessary for patient care. Likewise, current systems and methods do not allow a user to input, such intentional changes to electrode placement into the system in real-time so that the monitoring system can adjust its processing and analysis algorithms. Accordingly, the inventors devised the system and method disclosed herein, which detects changes from the expected lead placement and/or allows a user to input lead placement changes so that the correct algorithm is used to analyze spatial characteristics of cardiac signals, such as ECG signals.

In one embodiment, a method of monitoring a cardiac signal of a patient gathered through at least three electrodes connected to the patient according to an alternative electrode configuration is disclosed, wherein the alternative electrode configuration is a known electrode configuration that differs from a standard 12 lead ECG electrode configuration. The method comprises determining an alternative electrode configuration and automatically analyzing a cardiac signal based on the alternative electrode configuration.

In another embodiment an electrocardiograph system comprises a monitoring device capable of receiving cardiac signals from electrodes attached to a patient according to a known electrode configuration. The system further includes an analysis module configured to request information from the user identifying the known electrode configuration and automatically analyze the cardiac signals based on the known electrode configuration.

In yet another embodiment, a method of conducting ECG monitoring of the patient comprises acquiring a cardiac signal through electrodes connected to the patient according to a known electrode configuration and analyzing the cardiac signal to detect whether the known electrode configuration deviates from a standard 12 lead ECG configuration. If a deviation is detected, then an estimated electrode configuration for the electrodes connected to the patient is determined, and the estimated electrode configuration is presented to the user. Confirmation information is then requested from the user regarding whether the estimated electrode configuration is the known electrode configuration. The physiological data is the automatically analyzed based on the confirmation information.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
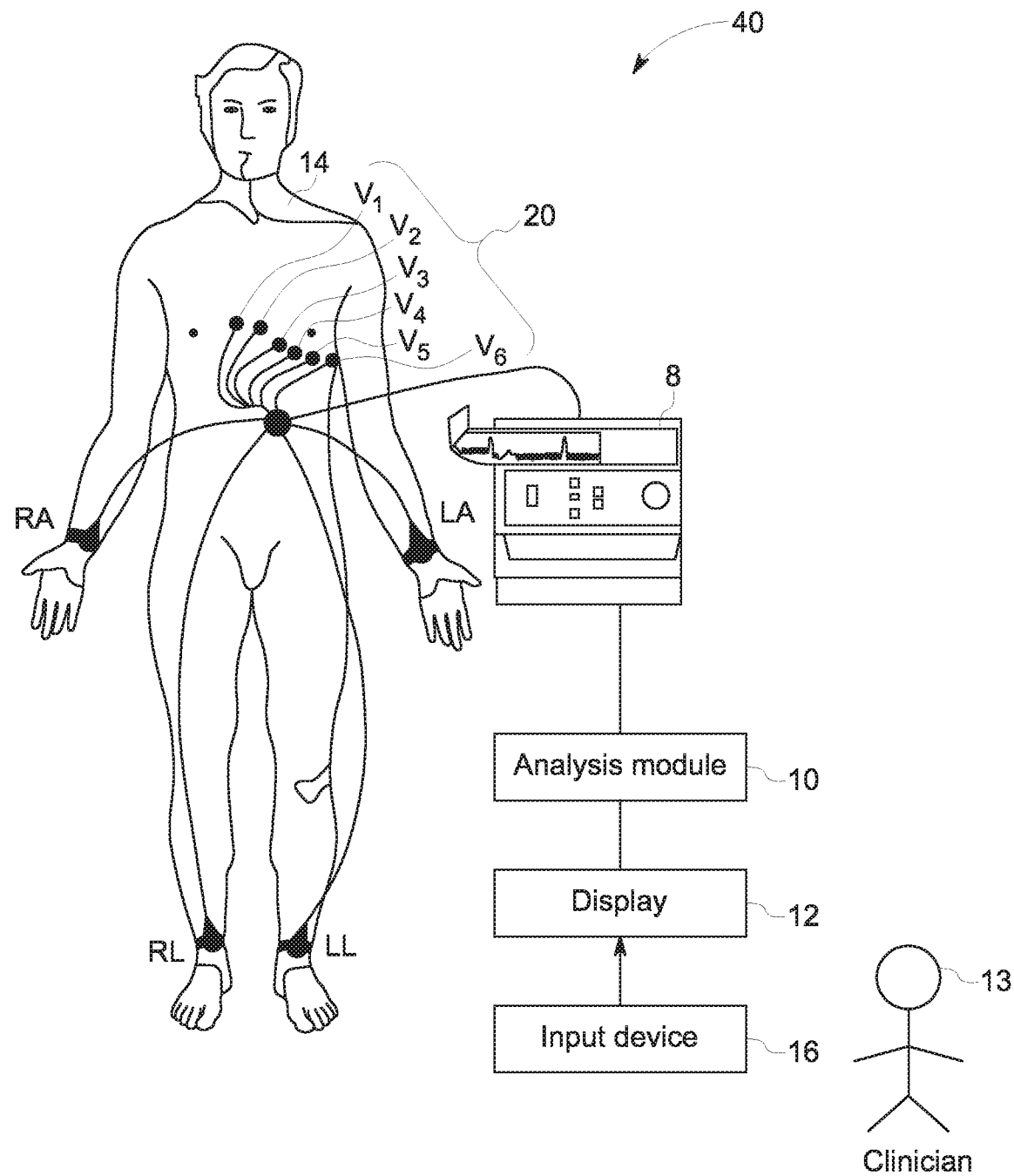
FIG. 1 provides the exemplary embodiment of a system for monitoring a patient's cardiac signal.

FIG. 1 depicts an exemplary system 40 for monitoring a patient's cardiac signal. Monitoring system 40 comprises a cardiac monitor 8, such as an ECG monitor, an analysis module 10, a display 12, and an input device 16 through which a user 13, such as a clinician, interacts with analysis module 10. More specifically, in the embodiment of FIG. 1, monitoring system 40 monitors patient cardiac signals employing an ECG monitor 8 receiving signal data from electrodes connected to patient 14. In the exemplary illustration of FIG. 1, ten electrodes are connected to patient 14 according to a standard 12 lead ECG configuration 20. The standard 12 lead ECG configuration 20 is one possible known electrode configuration out of many known electrode configurations. As described herein, there are numerous clinical reasons for which an alternative electrode configuration 23 (exemplified in FIGS. 4a-4c), which is a known electrode configuration other than a standard 12 lead ECG electrode configuration, may be used. In the standard 12 lead configuration 20, electrodes V1-V6, as well as the right arm electrode RA, left aim electrode LA, right leg electrode RL and left leg electrode LL are attached to the patient according to the standard 12 lead ECG configuration 20. The electrodes V1-V6, RA, LA, RL, and LL, record cardiac electrical signals from patient 14 and transmit those signals to ECG monitor 8. In the embodiment of FIG. 1, ECG monitor 8 then transmits the signals to analysis module 10.

One purpose of analysis module 10 is to analyze a cardiac signal, such as an ECG signal, and to detect whether a known electrode configuration of the electrodes on patient 14 differs from a default configuration of analysis module 10. The analysis module 10 may be configured to detect any known electrode configuration recognized in the art, or any subset thereof. Known electrode configurations include all standard, alternative, and otherwise recognized electrode configurations that are known in the art of cardiac monitoring, including nonstandard electrode configurations that are medically necessary given certain diagnoses or conditions of a patient. Known electrode configurations may include configurations having any number of electrodes or leads, including, without limitation, configurations having 8, 10, 12, or 14 electrodes. As described above, there are several reasons why a user 13 might use an alternative electrode configuration 23 when collecting cardiac data. For example, a user 13 may utilize a right chest electrode placement in which electrodes are placed on the right side of the chest. The right chest electrodes may be in placed on the patient in addition to the standard V2-V6 electrode placement, or the right chest electrode placement may involve moving some or all of the V2-V6 leads to the right side of the patient's 14 chest rather than the left side as in the standard 12 lead ECG electrode configuration (see FIGS. 4b-4c for illustrations of right chest electrode placement). In other embodiments the known electrode configuration may be a posterior electrode placement, or may include limb lead changes, such as a Mason-Likar (see FIG. 4a) arrangement, placing one or more of the limb electrodes RA, LA, RL, or LL onto the patient's torso instead of on the patient's limb(s). Analysis module 10 may further analyze and interpret the cardiac signal, for example to detect certain known diseases and/or conditions. Analysis module 10 may then output an interpretive statement of the cardiac signal listing any determinations made at the analysis stage.

In still other embodiments alternative electrode placement 23 may include nonstandard placements that are medically necessary or required, such as adjustment of one or more electrodes to accommodate a patient's 14 condition or injury. To provide one specific example, a user 13 administering an ECG to a patient with a left-side injury to their 6$^{th}$ rib may not be able to utilize a, standard 12 lead ECG electrode configuration and may creed to use an alternative configuration wherein the V4 and V5 lead are moved. The analysis module 10 may detect such a change from the standard 12 lead ECG electrode configuration and may automatically analyze the cardiac signal based on the alternative electrode placement 23. For example, the analysis module 10 may use a different set of criteria for assessing the cardiac signals recorded from the alternative electrode placement 23. If appropriate, the analysis module 10 may perform a reduced analysis and produce a reduced set of interpretations that discounts or ignores data, or a subset thereof, from certain electrodes.

In one exemplary embodiment pertaining to ECG, the default configuration is a standard 12 lead ECG configuration 20, and thus the analysis module determines whether the known electrode configuration is an alternative electrode configuration 23—i.e., a configuration that is different from the standard 12 lead ECG configuration 20. For example, the known electrode configuration depicted in FIG. 1 is standard 12 lead ECG configuration 20. If the default configuration for analysis module 10 is also standard 12 lead ECG configuration 20, then analysis module 10 would analyze the cardiac signal to determine that the known electrode configuration is equal to the default configuration. Analysis module 10 may then output an interpretive statement interpreting the cardiac signal accordingly. In other embodiments, the known electrode configuration is an alternative electrode configuration 23 that differs from the default configuration and analysis module 10 must determine the known electrode configuration, either by prompting the user for identification of the known electrode configuration or by estimating it based on analysis of the cardiac signal.

Figure 2:
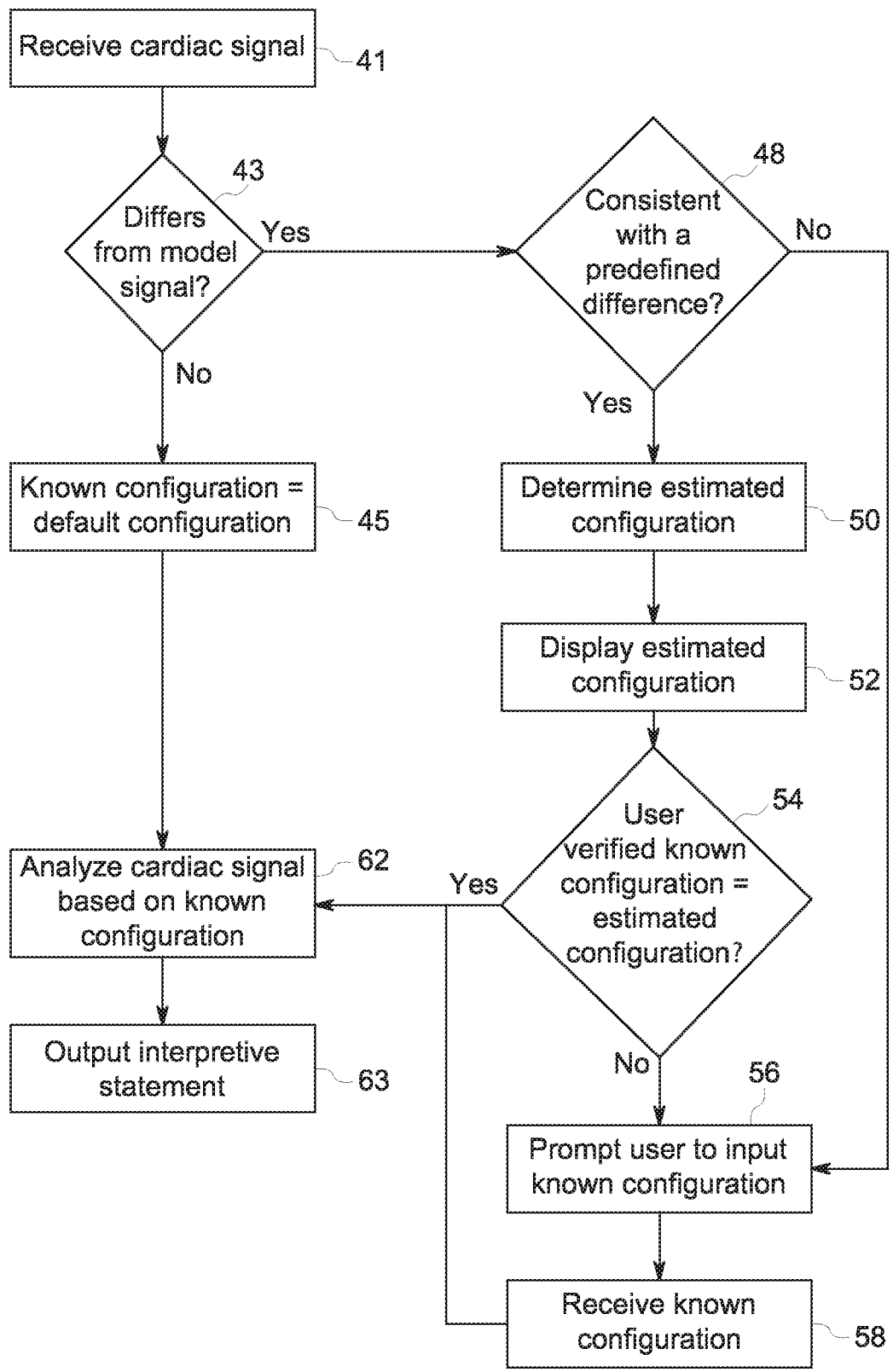
FIG. 2 provides an exemplary embodiment of a method for monitoring a patient's cardiac signal.

FIG. 2 depicts one exemplary embodiment of a method of monitoring a patient, which is one exemplary embodiment of a method that may be executed by analysis module 10. A cardiac signal is received at step 41. The cardiac signal may be, for example, a cardiac signal recorded by ECG electrodes. Then, at step 43, analysis module 10 determines whether the cardiac signal differs from a model signal associated with a default configuration. For example, the default configuration could be standard 12 lead ECG electrode configuration 20. In an alternative embodiment, the model signal may be a previous recording from patient 14 taken at an earlier time using a previous electrode configuration, and the analysis module 10 may set the default configuration as the previous configuration. In such an embodiment, the model signal would be a recording from patient 14 using an electrode configuration that is identifiable by the system. In an exemplary instance, the model signal may be a previous ECG recording taken from the patient using a standard 12 lead ECG electrode configuration 20 and, accordingly, the default configuration may be set as standard 12 lead ECG electrode configuration 20. In an alternative embodiment, the previous ECG recording may be taken from the patient using any known electrode configuration and the default configuration may be set to correspond to that particular known electrode configuration. In still other embodiments, the model signal may be an exemplary reference signal identifying common features present in a typical signal taken according to a default configuration. In such an embodiment, the model signal may present a range of acceptability for determining that the known electrode configuration 20 connected to the patient 14 matches the default configuration used by the analysis module 10.

In one exemplary embodiment, the analysis module 10 may employ matrix mathematics at step 43 to analyze each of the cardiac signal and the model signal, and thereby to determine whether they differ from one another in any significant way. More specifically, the analysis module 10 may employ the Karhunen-Loeve transform (KLT), singular value decomposition, principal components analysis, or principal forces analysis, to discover a set of basis vectors or eigenvectors that organize the variability of data in a multidimensional space along new directions, orthogonal to each other and ranked in order of significance. For each eigenvector, a corresponding eigenvalue is calculated. In addition, eigenvalue coefficients are calculated which correspond to the portion of each eigenvector that is necessary to reconstruct each original lead vector recorded between two electrodes. From the eigenvalue solution of the covariance matrix, the angles between the eigenvectors and the original vectors are determined. The eigenvalue coefficients and the angles between the eigenvectors and the original vectors are related by a cosine relationship. The angles calculated for each of the cardiac signal and the model signal can be compared to determine whether the electrodes are placed in the default ECG electrode configuration or a different known electrode configuration. In one alternative embodiment, the model signal may be a reference set of angles to which the angles calculated for the cardiac signal can be compared.

If the cardiac signal does not differ from the model signal at step 43 then analysis module 10 sets the known configuration as the default configuration. For example, in the embodiment depicted in FIG. 1 where the known configuration is a standard 12 lead ECG electrode configuration 20 and the default configuration is also the standard 12 lead ECG configuration 20, the known configuration is equal to the default configuration and thus would be correctly set at step 45. On the other hand, at step 43 if the cardiac signal differs from the model signal, then analysis module 10 proceeds to step 48 where it determines whether the difference between the cardiac signal and the model signal is consistent with one of a predefined set of differences. For instance, referring again to an ECG embodiment where the default configuration is the standard 12 lead ECG configuration 20, step 48 checks to see if the cardiac signal is different from the model signal in a way that is consistent with a known configuration. For example, if one or more of the signals associated with the leads is flipped up-side-down that may indicate that the known electrode configuration 20 of the electrodes attached to the patient 14 is a right chest electrode configuration wherein one or more of the V2-V6 electrodes is moved to the right side of the chest (such as shown in FIGS. 4b-4c).

In one embodiment, the analysis module 10 has a predefined set of differences between the default configuration and a list of known electrode configurations 20. The predefined set of differences may be, for example, a database or list of possible differences between a model signal associated with a default configuration and each of a set of known signals associated with a set of known electrode configurations. If the difference between the model signal and the cardiac signal is consistent with one of the predefined differences in the set of predefined differences at step 48, then analysis module 10 progresses to step 50 where it deter the estimated electrode configuration. The estimated electrode configuration is determined as the configuration associated with the difference detected between the cardiac signal and the model signal. As mentioned above, this difference may be determined by comparing the difference between the cardiac signal and the model signal to a set of predefined differences, where each of the predefined set of differences is associated with a known electrode configuration. Thus, the estimated electrode configuration may be the known electrode configuration associated with the difference between the cardiac signal and the model signal.

At step 54 the estimated electrode configuration is then presented to the user for verification. The user verification may be conducted by any user interface means known in the art. In one embodiment, the estimated electrode configuration is presented to the user along with the option to confirm or reject the estimated electrode configuration as the known configuration of electrodes placed on the patient 14. If the user confirms that the estimated electrode configuration is equal to the known electrode configuration, then the analysis module 10 progresses to step 62 where it analyzes the cardiac signal based on the known electrode configuration. The analysis module 10 may be configured to automatically perform such analysis of the cardiac signal to account for the known electrode configuration, such as by automatically selecting and executing corresponding and appropriate analysis algorithms.

On the other hand, if the user rejects the estimated configuration, stating that the known configuration is not equal to the estimated configuration, the analysis module 10 proceeds to step 56 where it prompts the user to input the known electrode configuration. Likewise, if the difference between the cardiac signal and the model signal is not consistent with a predefined difference, then analysis module 10 may progress from step 48 to step 56 where it prompts a user 13 to input the known electrode configuration. For example, analysis module 10 may display a graphic demonstrating the default electrode configuration or the estimated electrode configuration on the display 12, wherein the placement of one or more of the electrodes represented on the graphic may be adjusted by the user 13. In such an embodiment the user 13 may be prompted to adjust the configuration on the display 12 to represent the known electrode configuration. In another embodiment the analysis module 10 may request that the user identify the known electrode configuration by name or otherwise describe the known electrode configuration. In still other embodiments the analysis module may provide a list of possible known electrode configurations, such as a drop-down list and the user may select one configuration off of the list.

Once the user 13 enters information identifying the known electrode configuration and such information is received, analysis module 10 analyses the cardiac information based on the known electrode configuration at step 62. Lastly, at step 63 the analysis module 10 may output an interpretive statement. The interpretive statement may, for example list any abnormalities or disease indicators detected in the cardiac signal by the analysis module 10. Alternatively or additionally, the interpretive statement may provide an estimated or predicted diagnosis. Additionally, the analysis module 10 may store on a storage medium the cardiac signal in association with the known electrode configuration and/or the interpretive statement.

Figure 3:
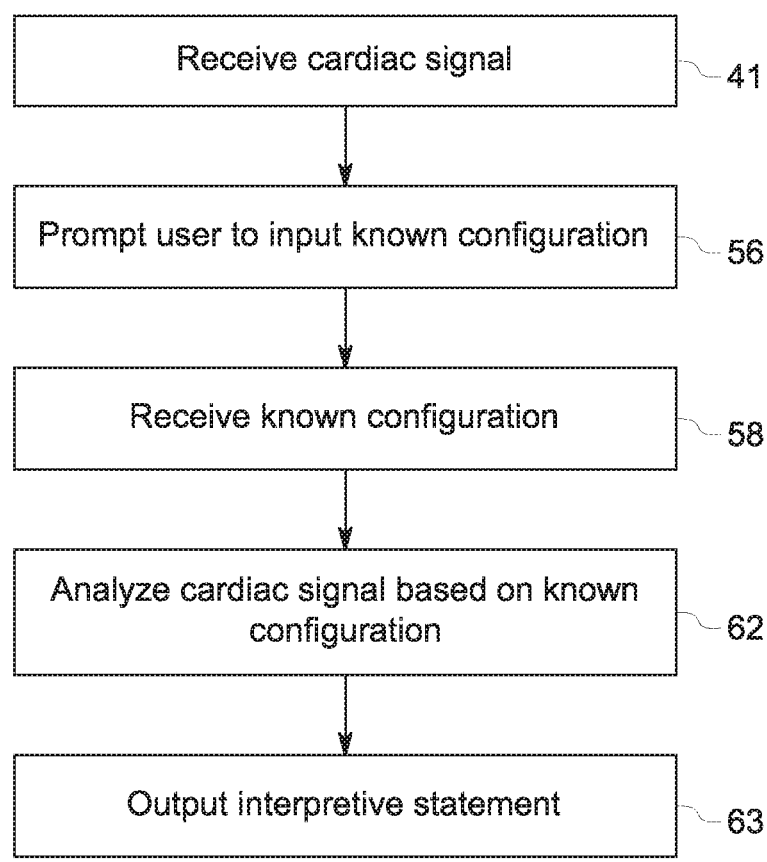
FIG. 3 provides another exemplary embodiment of a method for monitoring a patient's cardiac signal.

Turning to FIG. 3, another embodiment of a method of monitoring the cardiac signal of a patient is demonstrated. At step 41, a cardiac signal is received, for example via at least three electrodes connected to the patient according to a known electrode configuration. The user is then prompted to input the known electrode configuration at step 56. As described above with respect to step 56, the user may be prompted to input the known electrode configuration by any means known in the art. Once the user inputs the known electrode configuration, analysis module 10 receives the known electrode configuration at step 58 and then analyzes the cardiac signal at step 62 based on that known electrode configuration. The analysis module 10 then outputs an interpretive statement 63.

In still other embodiments, a method of monitoring the cardiac signal of a patient may include receiving a cardiac signal recorded from a patient using a known electrode configuration and then comparing it to a model signal to determine whether the known electrode configuration differs from the default configuration (see steps 41 and 43 of FIG.

2). Then, if a difference is detected between the known configuration and the default configuration, the system may prompt the user to input the known electrode configuration (see step 56 of FIGS. 2-3). As described with respect to FIGS. 2 and 3 above, once the user inputs the known electrode configuration, the analysis module 10 receives the known electrode configuration (step 58), analyzes the cardiac signal (step 62) based on that known electrode configuration, and then outputs an interpretive statement (step 63).

Figure 4A:
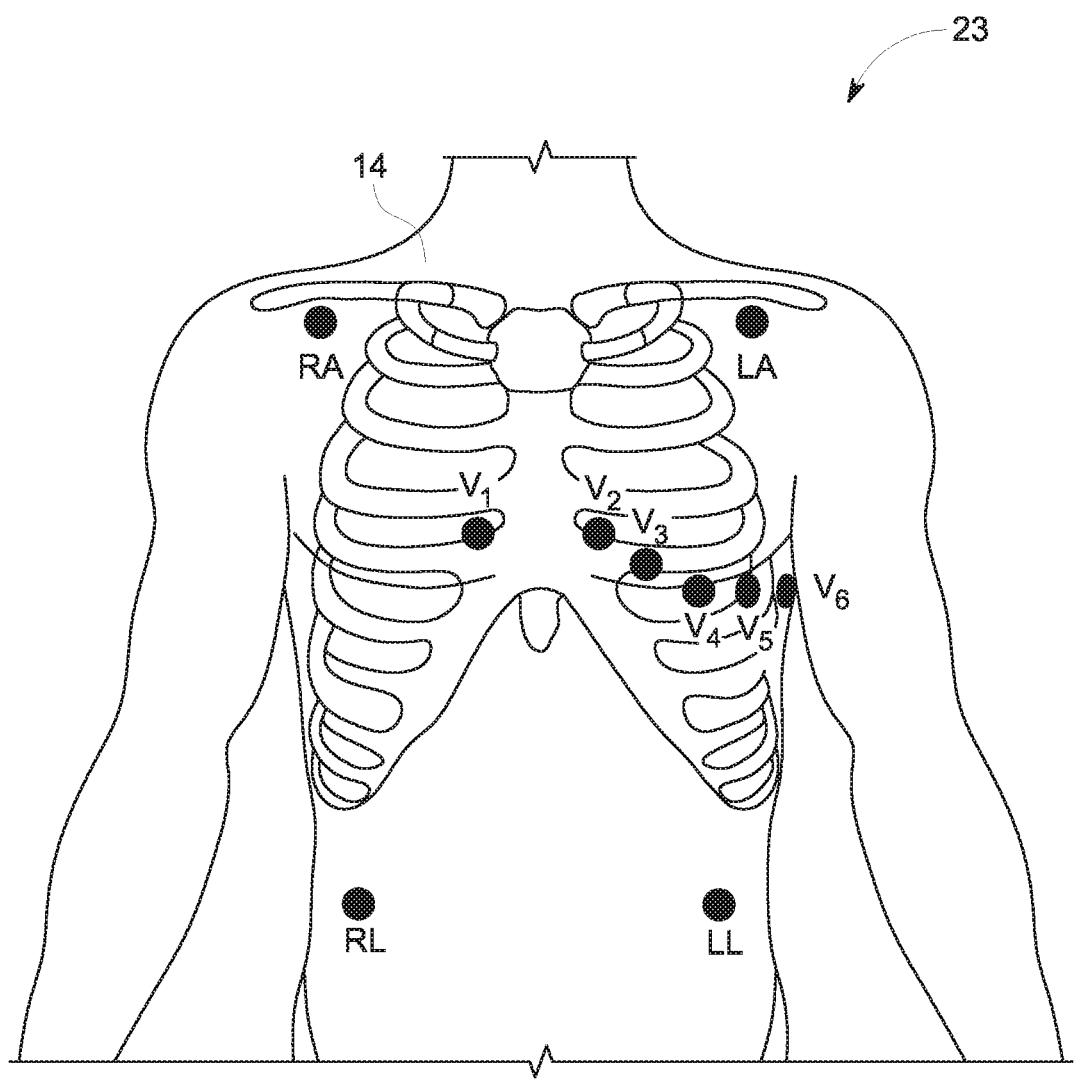
FIGS. 4*a*-4*c* provide illustrations of exemplary alternative electrode configurations for electrocardiography.
Figure 4B:
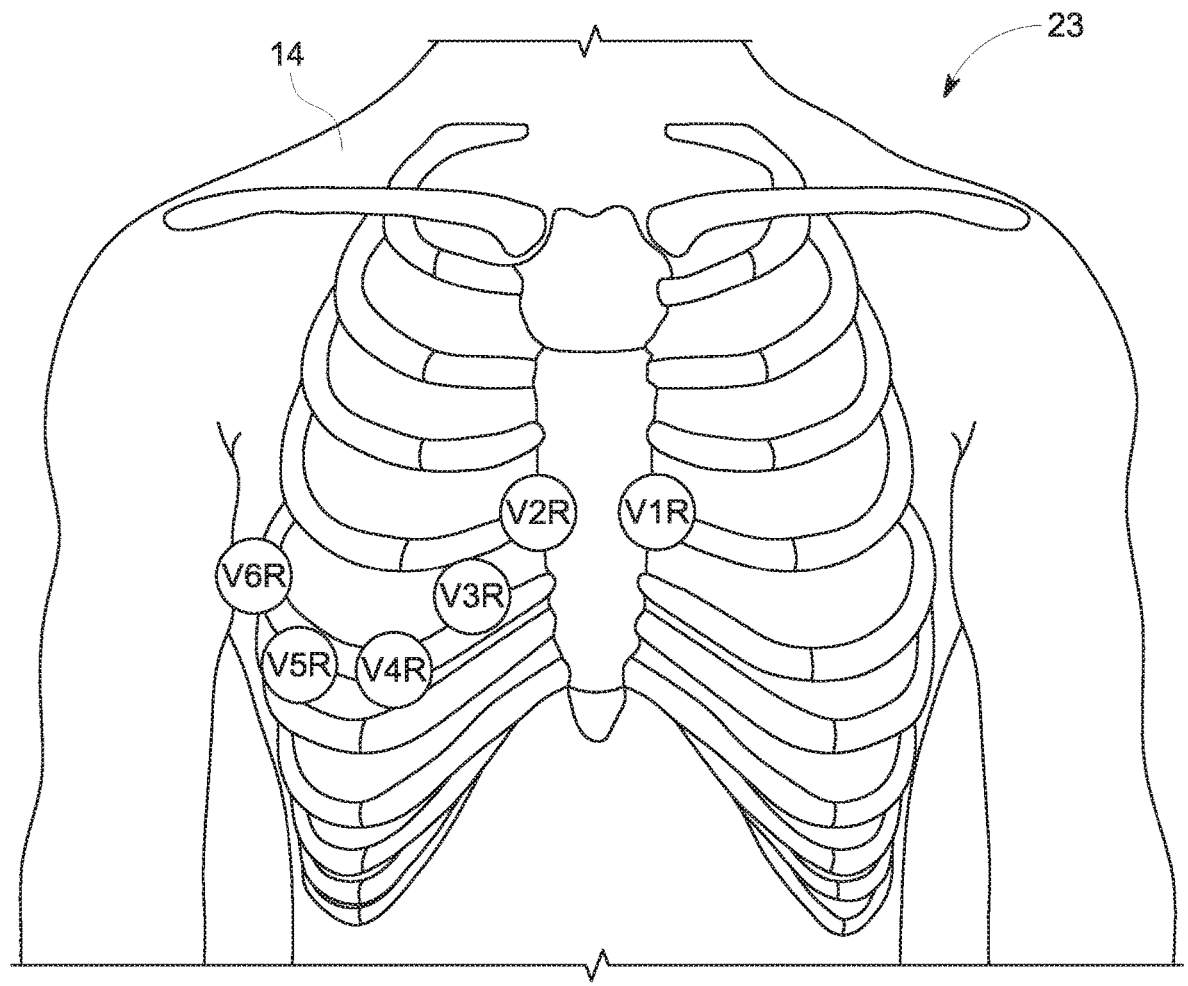
Figure 4C:
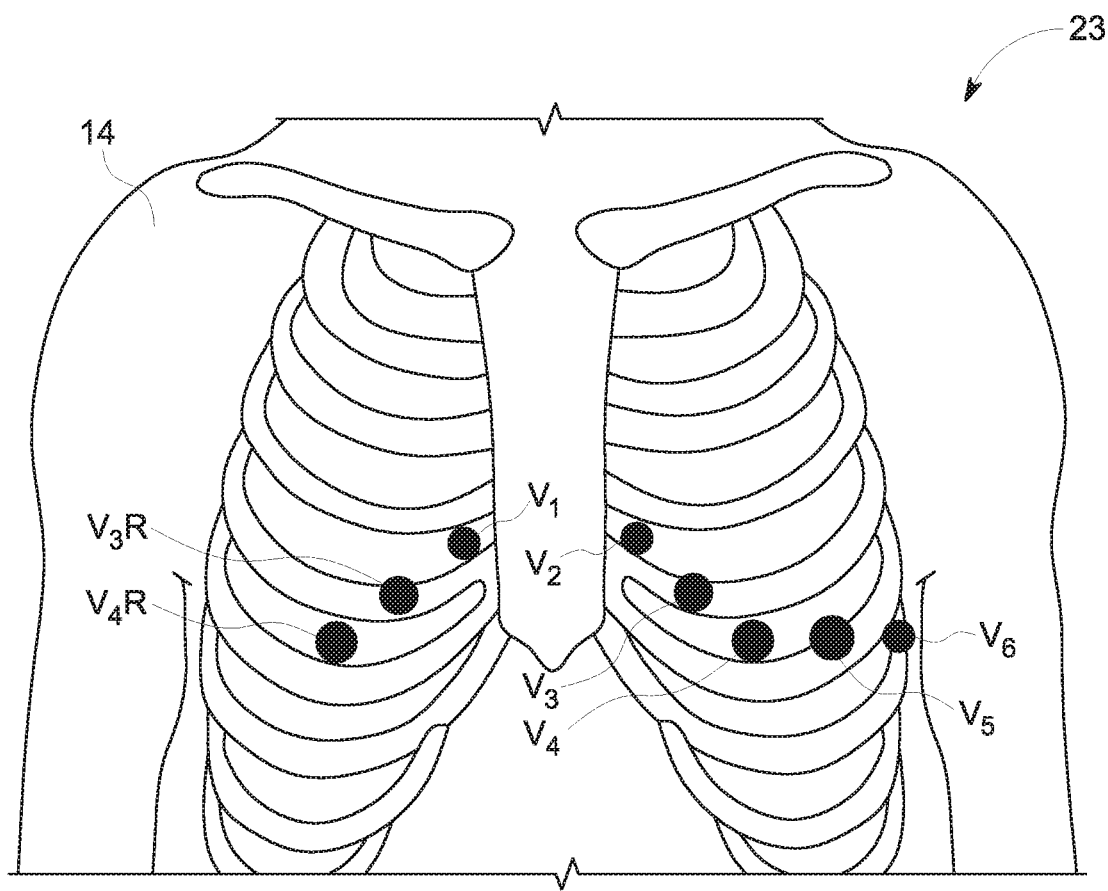

FIGS. 4a, 4b, and 4c illustrate just a few of the possible alternative electrode configurations 23, which are known electrode configurations other than the standard 12 lead electrode configuration 20. FIG. 4a demonstrates a Mason-Likar configuration. In the Mason-Likar configuration, the limb electrodes, including the, right arm electrode RA, the left arm electrode LA, the right leg electrode RL and the left leg electrode LL, are moved into the torso of the patient 14. For maximal accuracy in analyzing the cardiac signal, the analysis module 10 preferably is able to detect the Mason-Likar configuration and to analyze the cardiac signal accordingly.

FIGS. 4b and 4c illustrate two possible embodiments of a right chest electrode placement. In a right chest electrode placement, one or more of the electrodes V2-V6 is moved to the right side of the chest. Such a configuration may be clinically called for when monitoring certain patients, such as pediatric patients, or patients with dextrocardia. In FIG. 4b, the right chest electrode placement includes right placement of all of the V2-V6 electrodes, which are labeled as V2r, V3r, V4r, V5r, and V6r. Since the V2 electrode is moved to the right side, V2r, the V1 electrode is moved to the left side, and is also labeled V1r. FIG. 4c demonstrates a different right chest electrode placement wherein additional electrodes are placed on the right side of the chest in addition to the V1-V6 electrodes placed on the left side of the patient's 14 chest. Thus, in the embodiment of FIG. 4c, twelve electrodes are used to monitor the patient instead of ten electrodes. Alternatively, the V3 and V4 electrodes could be moved to the right side to become the V3r and V4r electrodes, respectively. In such an embodiment, only ten electrodes would be used. In the embodiments depicted in 4b and 4c, the limb electrodes may be placed on the limbs as shown in FIG. 1, or on the torso as shown in FIG. 4a. Preferably, the analysis module 10 would accurately determine such placement of the limb electrodes.

Figure 5:
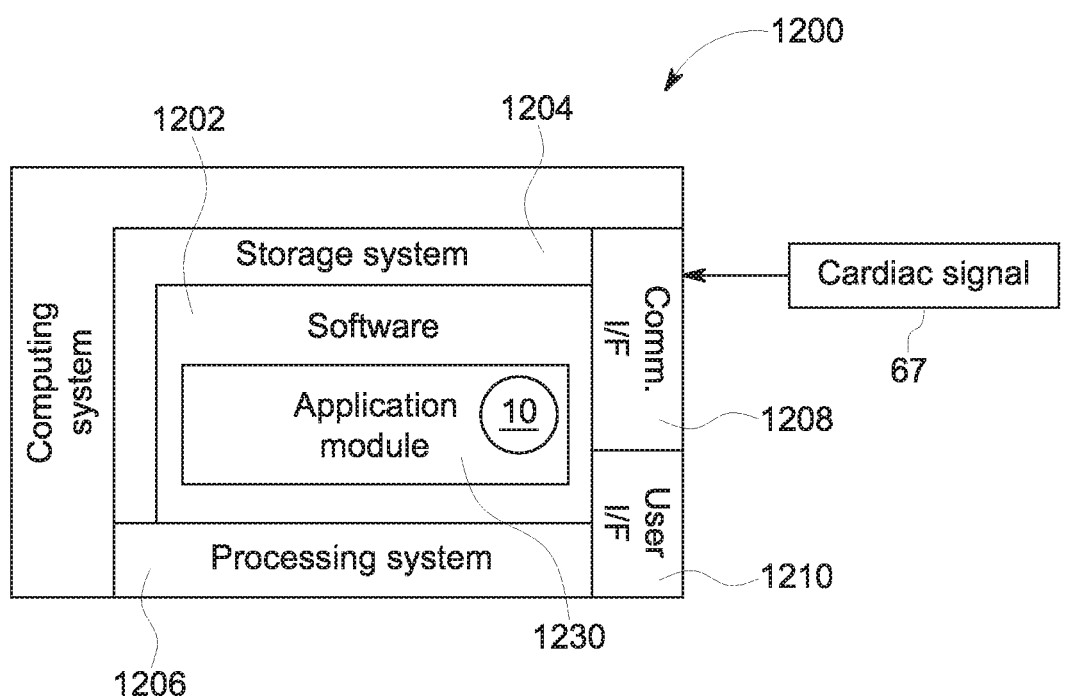
FIG. 5 depicts one embodiment of a system for executing a method for monitoring a patient's cardiac signal.

FIG. 5 is a system diagram of an exemplary embodiment of a system 1200 for implementing an analysis module 10. The system 1200 is generally a computing system that includes a processing system 1206, storage system 1204, software 1202, communication interface 1208 that interfaces with exterior devices, such as the monitoring device that may provide the cardiac signal 67, and a user interface 1210. The processing system 1206 loads and executes software 1202 from the storage system 1204, including application module 1230. When executed by the computing system 1200, application module 1230 directs the processing system 1206 to operate as described in herein in further detail, including execution of the analysis module 10. The application module 1230 and/or the analysis module 10 may further instruct the system to store analysis data produced by the analysis module 10 in the storage system 1204. For example, the analysis module 10 may instruct storage of the cardiac signal along with the known electrode configuration and/or the interpretive statement in the storage system 1204.

Although the computing system 1200 as depicted in FIG. 7 includes one software module 1202 in the present example, it should be understood that one or more modules could cooperate to provide the same operation. Similarly, while description as provided herein refers to a computing system 1200 and a processing system 1206, it is to be recognized that implementations of such systems can be performed using one or more processors, which may be communicatively connected, and such implementations are considered to be within the scope of the description.

The processing system 1206 can comprise a microprocessor and other circuitry that retrieves and executes software 1202 from storage system 1204. Processing system 1206 can be implemented within a single processing device but can also be distributed across multiple processing devices or sub-systems that cooperate in existing program instructions. Examples of processing system 1206 include general purpose central processing units, applications specific processors, and logic devices, as well as any other type of processing device, combinations of processing devices, or variations thereof.

The storage system 1204 can comprise, any storage media readable by processing system 1206, and capable of storing software 1202 and other data. The storage system 1204 can include volatile and non-volatile, removable and non-removable media implemented in any method or technology for storage of information, such as computer readable instructions, data structures, program modules, or other data. Storage system 1204 can be implemented as a single storage device but may also be implemented across multiple storage devices or sub-systems. Storage system 1204 can further include additional elements, such a controller capable, of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. In some implementations, the store media can be a non-transitory storage media. In some implementations, at least a portion of the storage media may be transitory. It should be understood that in no case is the storage media a propagated signal.

User interface 1210 can include a mouse, a keyboard, a voice input device, a touch input device for receiving a gesture from a user, a motion input device for detecting non-touch gestures and other motions by a user, and other comparable input devices and associated processing elements capable of receiving user input from a user. Output devices such as a video display or graphical display can display an interface further associated with embodiments of the system and method as disclosed herein. Speakers, printers, haptic devices and other types of output devices may also be included in the user interface 1210.

As described herein, the computing system 1200 receives cardiac signal 67 through the communication interface 1208. The cardiac signal 67 may be, for example, an ECG recording from three or more leads attached to the patient 14. In still further embodiments, the cardiac signal 67 may be streaming data received in real time or near-real time by the computing system 1200, or the cardiac signal 67 may be a previously recorded signal sent to the computing system 1200 for processing.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. An electrocardiograph (ECG) system, the ECG system comprising:
    a monitoring device configured to receive cardiac signals from electrodes attached to a patient in an alternative electrode configuration, wherein the alternative electrode configuration is one of a predetermined set of known electrode configurations that differs from a specific default configuration;
    a display and an input device connected to the display;
    an analysis module configured to:
        analyze the cardiac signals to detect that the electrodes are attached to the patient in an electrode configuration that differs from the default configuration;
        determine an estimated electrode configuration, wherein the estimated electrode configuration is one of the predetermined set of electrode configurations;
        display a graphical depiction of the estimated electrode configuration on the display, wherein the graphical depiction includes a graphic for each electrode in the estimated electrode configuration, wherein each graphic for each electrode is movable on the display by a user;
        receive input from the user regarding the estimated electrode configuration and/or the alternative electrode configuration, wherein the input includes a movement on the display of one or more of the graphics for the electrodes;
        determine the alternative electrode configuration based on the input;
        automatically retrieve ECG analysis criteria for assessing the cardiac signals based on the alternative electrode configuration; and
        automatically analyze the cardiac signals based on the ECG analysis criteria for the alternative electrode configuration.

2. The system of claim 1 wherein the analysis module analyzes the cardiac signals by comparing at least one of the cardiac signals to a model signal associated with the default configuration to determine that the electrode configuration differs from the default configuration.

3. The system of claim 2 wherein the system is configured to store the cardiac signals in a storage system with reference to the alternative electrode configuration; and
    wherein the model signal includes at least one previously recorded cardiac signal from the patient, wherein the previously recorded cardiac signal from the patient is associated with at least one known electrode configuration in the predetermined set of known electrode configurations.

4. The system of claim 2 wherein the default configuration is a standard 12 lead ECG electrode configuration, and the model signal is a cardiac signal associated with the standard 12 lead ECG electrode configuration.

5. A method of conducting electrocardiograph (ECG) monitoring of a patient, the method comprising:
    acquiring at least one cardiac signal through electrodes on the patient;
    analyzing the cardiac signal to detect that the electrodes are arranged on the patient according to an electrode configuration that differs from a standard 12 lead ECG configuration;
    determining an estimated electrode configuration, wherein the estimated electrode configuration is one of a predetermined set of known electrode configurations that differs from a standard 12 lead ECG configuration;
    displaying a graphical depiction of the estimated electrode configuration on a display, wherein the graphical depiction includes a graphic for each electrode in the estimated electrode configuration, wherein each graphic for each electrode is movable by a user;
    receiving information from the user regarding the estimated electrode configuration, wherein the information received from the user includes a movement of one or more of the graphics for the electrodes;
    identifying an alternative electrode configuration based on the movement of the one or more of the graphics for the electrodes, wherein the alternative electrode configuration is one of the predetermined set of known electrode configurations that differs from a standard 12 lead ECG configuration; and
    automatically analyzing the cardiac signal acquired from the patient based on the information.

6. The method of claim 5 wherein the step of determining an estimated electrode configuration includes selecting one of the predetermined set of known electrode configurations based on the cardiac signal.

7. The method of claim 5 wherein the step of analyzing the cardiac signal includes comparing the cardiac signal to a model signal to determine whether the cardiac signal differs from the model signal.

8. The method of claim 7 wherein the estimated electrode configuration is determined based on the difference between the cardiac signal and the model signal.

9. The method of claim 8 wherein the step of analyzing the cardiac signal further includes determining whether the difference between the cardiac signal and the model signal is consistent with any of a predefined set of differences, wherein each difference in the predefined set of differences corresponds with a possible difference between a model signal associated with a default configuration and each of a set of known signals associated with the predetermined set of known electrode configurations.

10. The method of claim 9 wherein determining whether the difference between the cardiac signal and the model signal is consistent with any of a predefined set of differences includes determining whether the difference between the cardiac signal and the model signal is consistent with a right chest electrode placement.

11. The method of claim 7 wherein the model signal is a previously recorded cardiac signal from the patient, wherein the previously recorded cardiac signal from the patient is associated with a previous known electrode configuration.

12. The method of claim 5 further comprising retrieving a set of criteria for assessing the at least one cardiac signal based on the alternative electrode configuration; and
    analyzing the at least one cardiac signal based on the set of criteria for the alternative electrode configuration.

13. An electrocardiograph (ECG) system, the ECG system comprising:
    a monitoring device configured to receive cardiac signals from electrodes attached to a patient in an alternative electrode configuration, wherein the alternative electrode configuration is one of a predetermined set of known electrode configurations that differs from a specific default configuration;

a display;

an analysis module configured to:

analyze the cardiac signals to detect that the electrodes are attached to the patient in an electrode configuration that differs from the default configuration;

display a list containing at least one of the predetermined set of known electrode configurations, wherein each electrode configuration of the predetermined set of known electrode configurations is selectable by a user;

receiving input from a user via an input device selecting one of the predetermined set of known electrode configurations in the list;

determining the alternative electrode configuration based on the input from the user;

automatically retrieve ECG analysis criteria for assessing the cardiac signals based on the alternative electrode configuration; and automatically analyze the cardiac signals based on the ECG analysis criteria for the alternative electrode configuration.

14. The system of claim 13 wherein the analysis module analyzes the cardiac signals by comparing at least one of the cardiac signals to a model signal associated with the default configuration to determine that the electrode configuration differs from the default configuration.

15. The system of claim 14 wherein the system is configured to store the cardiac signals in a storage system with reference to the alternative electrode configuration; and wherein the model signal includes at least one previously recorded cardiac signal from the patient, wherein the previously recorded cardiac signal from the patient is associated with at least one known electrode configuration in the predetermined set of known electrode configurations.

16. The system of claim 14 wherein the default configuration is a standard 12 lead ECG electrode configuration, and the model signal is a cardiac signal associated with the standard 12 lead ECG electrode configuration.

* * * * *